(12) United States Patent
Dasek et al.

(10) Patent No.: US 11,864,782 B2
(45) Date of Patent: Jan. 9, 2024

(54) SHOCK WAVE DEVICE

(71) Applicant: BTL Medical Technologies S.R.O., Prague (CZ)

(72) Inventors: Jiri Dasek, Soprec u Prelouce (CZ); Tomas Schwarz, Prague (CZ)

(73) Assignee: BTL Medical Solutions A. S., Prague (CZ)

( * ) Notice: Subject to any disclaimer, the term of this patent is extended or adjusted under 35 U.S.C. 154(b) by 806 days.

(21) Appl. No.: 16/205,401

(22) Filed: Nov. 30, 2018

(65) Prior Publication Data

US 2019/0159794 A1 May 30, 2019

Related U.S. Application Data

(60) Provisional application No. 62/592,464, filed on Nov. 30, 2017.

(51) Int. Cl.
| | | |
|---|---|---|
| *A61N 7/00* | (2006.01) |
| *A61B 17/225* | (2006.01) |
| *B06B 1/06* | (2006.01) |
| *G10K 9/122* | (2006.01) |
| *G10K 11/02* | (2006.01) |
| *G10K 11/30* | (2006.01) |

(Continued)

(52) U.S. Cl.
CPC ............ *A61B 17/2251* (2013.01); *A61N 7/00* (2013.01); *B06B 1/0644* (2013.01); *G10K 9/122* (2013.01); *G10K 11/02* (2013.01); *G10K 11/30* (2013.01); *G10K 15/043* (2013.01); *A61B 17/225* (2013.01); *A61B 18/12* (2013.01); *A61B 2017/22027* (2013.01); *A61B 2018/00994* (2013.01); *A61N 2007/006* (2013.01); *A61N 2007/0056* (2013.01)

(58) Field of Classification Search
CPC .... A61N 2007/0004–0034; A61N 7/00; A61N 7/02; B06B 1/0644; G10K 11/02; G10K 11/30; G10K 15/043; G10K 9/122; A61H 23/008
See application file for complete search history.

(56) References Cited

U.S. PATENT DOCUMENTS

| | | | |
|---|---|---|---|
| 4,721,874 A * | 1/1988 | Emmert | G01N 11/00 310/333 |
| 4,858,597 A | 8/1989 | Kurtze | |

(Continued)

FOREIGN PATENT DOCUMENTS

| | | |
|---|---|---|
| CN | 201664476 | 12/2010 |
| CN | 203598376 | 5/2014 |

(Continued)

OTHER PUBLICATIONS

C600, Operator Manual, 35 p., 2019.

(Continued)

*Primary Examiner* — Amelie R Davis
(74) *Attorney, Agent, or Firm* — Riverside Law LLP

(57) ABSTRACT

A device for shock wave production to treat a patient's body comprises a base with a condenser as power supply, an applicator having a pad, at least one piezo-element configured to generate a shock wave in response to a pulse of electric current having a pulse width, an acoustic lens configured to focus the shock wave, and a coil configured to increase the pulse width of the pulse of electric current.

32 Claims, 6 Drawing Sheets

(51) Int. Cl.
  *G10K 15/04* (2006.01)
  *A61B 17/22* (2006.01)
  *A61B 18/00* (2006.01)
  *A61B 18/12* (2006.01)

(56) References Cited

U.S. PATENT DOCUMENTS

| | | | |
|---|---|---|---|
| 5,076,277 A * | 12/1991 | Iwama | A61B 17/2256 601/4 |
| 5,387,190 A * | 2/1995 | Gotanda | A61B 17/22012 604/22 |
| 5,501,655 A * | 3/1996 | Rolt | A61N 7/02 600/439 |
| 5,545,124 A * | 8/1996 | Krause | A61N 7/00 601/2 |
| 5,873,845 A * | 2/1999 | Cline | A61N 7/02 601/3 |
| 6,036,661 A | 3/2000 | Schwarze | |
| 6,113,559 A | 9/2000 | Klopotek | |
| 6,325,769 B1 | 12/2001 | Klopotek | |
| 6,368,292 B1 | 4/2002 | Ogden | |
| 6,416,478 B1 * | 7/2002 | Hossack | B06B 1/064 600/459 |
| 6,736,784 B1 | 5/2004 | Menne | |
| 6,755,796 B2 | 6/2004 | Spector | |
| 7,189,209 B1 | 3/2007 | Ogden | |
| 8,568,339 B2 | 10/2013 | Rybyanets | |
| 10,743,838 B2 * | 8/2020 | Freiburg | A61B 17/2251 |
| 2002/0193709 A1 | 12/2002 | Bolze | |
| 2004/0010211 A1 | 1/2004 | Spector | |
| 2004/0015107 A1 | 1/2004 | Du | |
| 2004/0036555 A1 | 2/2004 | Fehre | |
| 2004/0167445 A1 | 8/2004 | Simnacher | |
| 2005/0010140 A1 | 1/2005 | Forssmann | |
| 2005/0015023 A1 | 1/2005 | Ein-Gal | |
| 2005/0148911 A1 | 7/2005 | Talish | |
| 2005/0154431 A1 | 7/2005 | Quistgaard | |
| 2005/0192556 A1 * | 9/2005 | Soltani | A61N 7/00 604/500 |
| 2006/0100550 A1 | 5/2006 | Schultheiss | |
| 2008/0146971 A1 | 6/2008 | Uebelacker | |
| 2009/0088670 A1 | 4/2009 | Warlick | |
| 2009/0156894 A1 | 6/2009 | Hagelauer | |
| 2009/0171252 A1 * | 7/2009 | Bockenstedt | G10K 11/352 601/2 |
| 2011/0066084 A1 | 3/2011 | Desilets | |
| 2011/0270139 A1 | 11/2011 | Bauer | |
| 2012/0029393 A1 * | 2/2012 | Lee | A61B 8/4444 601/2 |
| 2012/0157888 A1 * | 6/2012 | Grob | A61N 7/02 601/2 |
| 2013/0046210 A1 | 2/2013 | Zhong | |
| 2013/0096436 A1 * | 4/2013 | Little | G01S 7/5205 600/459 |
| 2013/0197404 A1 | 8/2013 | Spector | |
| 2013/0294203 A1 | 11/2013 | Goodman | |
| 2014/0024974 A1 | 1/2014 | Slayton | |
| 2015/0005638 A1 | 1/2015 | Slayton | |
| 2015/0177197 A1 | 6/2015 | Kojima | |
| 2015/0224345 A1 | 8/2015 | Warlick | |
| 2016/0001097 A1 | 1/2016 | Cho | |
| 2017/0043189 A1 * | 2/2017 | Stoddard | A61N 7/02 |
| 2019/0060675 A1 * | 2/2019 | Krone | A61N 7/02 |
| 2020/0206072 A1 * | 7/2020 | Capelli | A61B 18/203 |

FOREIGN PATENT DOCUMENTS

| | | |
|---|---|---|
| CN | 205054800 | 3/2016 |
| DE | 19949426 | 11/2001 |
| DE | 102007014245 | 9/2008 |
| DE | 202009011534 | 12/2010 |
| DE | 202010014057 | 4/2011 |
| EP | 0629993 | 12/1994 |
| EP | 1072226 | 1/2001 |
| EP | 1195167 | 4/2002 |
| EP | 1863569 | 12/2007 |
| EP | 1943998 | 7/2008 |
| EP | 2166963 | 3/2010 |
| EP | 2172159 | 4/2010 |
| EP | 2308397 | 4/2011 |
| EP | 2351530 | 8/2011 |
| EP | 2382924 | 11/2011 |
| EP | 2493434 | 9/2012 |
| EP | 2628456 | 8/2013 |
| EP | 3064157 | 9/2016 |
| EP | 3154633 | 4/2017 |
| EP | 3196221 | 7/2017 |
| JP | 2011188924 | 9/2011 |
| JP | 5557800 | 7/2014 |
| JP | 5975600 | 8/2016 |
| KR | 20080040111 | 5/2008 |
| KR | 101418356 | 7/2014 |
| KR | 101602820 | 3/2016 |
| KR | 101747817 | 6/2017 |
| TW | 201420213 | 6/2014 |
| WO | 2007108854 | 9/2007 |
| WO | 2009018406 | 2/2009 |
| WO | 2011138784 | 11/2011 |
| WO | 2013068569 | 5/2013 |

OTHER PUBLICATIONS

Chattanooga—Moving Rehabilitation Forward, Focus Shockwave Operating Manual, 100 p., 2016.
Schmitz, et al., "Efficacy and safety of extracorporeal shock wave therapy for orthopedic conditions: a systematic review on studies listed in the PEDro database", British Medical Bulletin vol. 116, Nov. 2015, pp. 115-138.
Storz Medical, Comparison of Shock Wave Technologies, 4 p., 2013.
Storz Medical, Duolith SD1 Application Brochure, 36 p., 2010.
Storz Medical, Duolith SD1 T-Top, 8 p., 2015.
Storz Medical, Duolith SD1, 16 p., 2005.
Storz Medical, Extracorporeal Shock Wave Therapy, 32 p., 2015.

* cited by examiner

SHOCK WAVE DEVICE

CROSS-REFERENCE TO RELATED APPLICATIONS

This application claims priority to U.S. Provisional Patent Application No. 62/592,464, filed Nov. 30, 2017, the entire contents of which is incorporated by reference.

FIELD OF THE INVENTION

The field of the invention is a device and method with a high degree of modularity including one piezo-element with long durability creating shock waves to treat body tissue.

BACKGROUND OF THE INVENTION

Shock waves are biphasic high-energy acoustic wave pulses. A shock wave may be defined as a rapid pressure increase in a region of a patient's tissue, having a duration in a range from 20 ns (nanoseconds) to 4 μs (microseconds). The pressure of a shock wave typically exceeds 5 MPa in the tissue region. A shock wave consists of at least one positive phase and at least one negative pulse phase. The positive phase usually consists of a rapid rise in pressure followed by a slower decrease in pressure in the tissue region. Pressure in the tissue region during the positive phase is equal or higher than the pressure in the tissue region before shock waves were applied. During the negative shock wave phase, pressure in the tissue region is lower than before the shock wave was applied.

Shock waves may be used to treat patients with pseudarthrosis, to treat bones and soft tissue injuries, to reduce chronical pain, or many other ailments.

Currently used devices may produce shock waves via, for example, ballistics, spark gap, electromagnetics, piezoelectrics, or some other mechanism. Each method of producing shock waves has advantages and disadvantages.

Devices producing shock waves using ballistics may need to be connected to a compressor that may make manipulation with the applicator harder. Such devices produce uncomfortable noise, and may also show excess wear on the treatment area after several thousand pulses. The contact surface of ballistic shock wave applicator heads are limited in size, and the ability to focus the generated shock wave is limited by the constraints inherent in shock wave excitation. Ballistic devices are not able to produce shock wave pressures as high as other types of shock wave applicators, for example piezoelectric applicators.

Spark gap shock waves are problematic because the spark source suffers from rapid wear of its components. Spark gap shock waves also require a complex acoustic lens and a spark source filled with fluid, that requires precise manufacturing in order to prevent leaks and to maintain the required purity of the fluid during use. The spark source in the treatment head produces a first unfocused shock wave and also a secondary shock wave reflected from the acoustic lens surface that may be focused. The delay between first and second shock wave may decrease treatment effect or may lead to unwanted side effects in the patient's tissue. Current devices also struggle to produce sparks of repeatable intensity, size, and depth, leading to shock wave pulses having different intensity, depth, size and shape of focus volume. Systems for controlling parameters of a spark gap shock wave are limited. Importantly, intensities of shock waves produced in this manner cannot be varied in a controlled manner during treatment.

Electromagnetic shock wave generators are limited in the range of pressures they can induce in a tissue region. Also, the pressure increase during the positive shock wave phase is slower than that of shock waves generated using other means. Electromagnetic shock wave generators also tend to overheat. The durability of such devices may be decreased as a result, and the service cost may be very high. The Above-mentioned insufficiencies of electromagnetic shock wave generators limit treatment effects and the durability of such devices.

Piezoelectrics shock wave generators are among the most controlled and variable methods of producing shock waves in a patient's body. However, current piezoelectric shock wave generators are not able to use one large piezo-element in the applicator's head because the forces acting a single piezo-element would be too large. Increasing the size of the piezo-element also increases the magnitude of the force generated, and so larger piezo elements are prone to breaking. Existing devices using a single piezo-element break after only a short period of use, for example several thousand pulses.

Existing devices solve durability problems with piezo-elements by using multiple small and synchronized piezo-elements instead of a single large one. However, attaching multiple piezo-elements to a single substrate is very complicated to manufacture and piezo-elements also tend to peel away from the substrate. This results in decreased output power and accuracy during the life of the device. Current state of the art devices using multiple small piezo-elements as a source of shock waves (for example with piezo-element diameter below 2 cm or surface area below 2 $cm^2$) show significantly decreasing efficiency during their lifetimes.

Another disadvantage of current state of the art piezo-elements relates to energy transfer from the applicator to a patient's tissue. Currently used devices improve energy transfer by phase shifted excitation of individual piezo-elements. Phase shifted excitation of individual piezo-elements may also be used to focus shock waves. Shock waves produced in this way may create inconsistent energy distribution in the tissue region. Additionally, fabrication of substrates containing multiple piezo-elements as shock wave sources may be very complicated and expensive. Synchronization of individual piezo-elements may cause further complications, and piezo-elements that become desynchronized may cause additional problems during use.

Another disadvantage of current piezoelectric shock wave generators is a short first period or full width at half maximum (FWHM) of the first peak in the time domain function describing the electric pulses (for example electric current or voltage) provided from the condenser to the piezo-elements. The FWHM of the first peak (for example current) may have a positive or negative value. A short first period or FWHM of in the electric pulse results in a high magnitude pressure value with a small focus volume, for example having a diameter of 0.7 mm, generated by the piezo-element. The energy pulse may be extended by slowing the release of electric energy accumulated in the condenser, but doing so results in significant energy loss and physical wear of condenser switching elements. Therefore, this technique is not typically used in the current state of the art.

Thus, there is a need in the art of shock wave generating devices for a durable, efficient applicator that can change focus volume size, shape or depth during a treatment without changing the amount of shock wave energy delivered to a patient, and without changing the applicator's treatment head. The current invention satisfies this need.

SUMMARY OF THE INVENTION

Some embodiments of a presented device and a method comprise one piezo-element fitted in the head of an applicator. The device may be used to treat body tissue by generating shock waves. Some embodiment of the device may include detection means to be able to recognize when one or more parts of the device have reached or will soon reach a critical threshold of wear.

According to one embodiment, the device comprises one piezo-element resistant to wear, and an inductance element with inductance (e.g.: a coil or inductor) to adjust the duration and magnitude of electric current provided to the piezo-element that generates shock waves. Different length and value of a shock wave excitation electric pulse changes shock wave parameters. Changed parameters may be e.g.: the focal volume, shape of the shock wave, superposition of acoustic waves in the applicator and/or pressure value of the shock wave. The electric current may be adjusted by changing inductance of the inductance element e.g.: by changing the inductance of the coil, or by changing the distance between the coil and the conductive plate above the piezo-element.

In one embodiment, the device allows adjusting the duration of the shock wave excitation electric pulse period, resulting in an increase in the shock wave focus volume, and therefore deeper shock wave penetration. Increasing the FWHM of the first peak of electric energy may also lead to improved energy transfer to the patient's body and increased device life. Increasing the period of the first peak may further allow for adjustment of shockwave parameters, for example focus volume size, shape, depth or intensity of the kinetic energy delivered to the patient's body.

Certain embodiments of the invention relate to innovative methods of attaching the piezo-element to the applicator's head. In one embodiment, the piezo-element is attached using a material with the appropriate tensile and flexural strength parameters, allowing for increased piezo-element durability. This increased durability means that a large piezo-element can be used with systems of the present invention than would otherwise be possible.

Furthermore, systems of the present invention include improvements to the materials used, acoustic lens design, and a unique mounting system for the piezo-element. These improvements reduce the costs of device fabrication, increase device durability, and also improve energy transfer from the applicator's head to the patient's body. One of the most unique properties of the device and the method may be to apply two shock waves generated by one shock wave excitation electric pulse. Wherein the second peak of the positive shock wave phase may have higher maximal values and may be amplified as a superposition of reflected waves in the applicator, where the applicator is configured to act as a resonator.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DEFINITIONS OF TERMS

Figure 1:
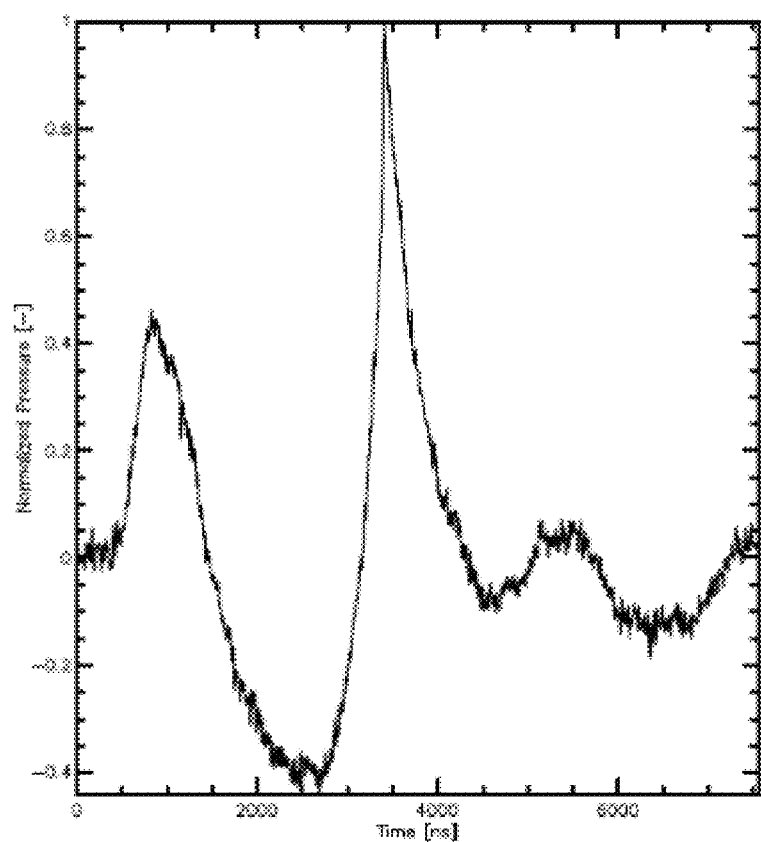
FIG. 1 depicts a shock wave graph of pressure vs. time generated by one possible applicator embodiment.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

An external device may refer to any device communicating with a device of the present invention. An external device may include a device used to guide at least part of the treatment process, or may enable the exchange of information between one or more devices of the present invention and, for example, systems or networks in the service or sale department of an apparatus provider. An external device may be any device providing any kind of energy to a device of the present invention, for example any treatment device able to communicate with the apparatus or wider system.

Attaching two parts means that the two different parts are in direct contact with one another, or are in close proximity to one another, having a minimum distance from one another that is less than 3 mm.

Focal volume, as used herein, refers to a volume into which a shock wave is delivered having a pressure equal to or higher than the FWHM (Full Width at Half Maximum)

pressure value produced by a piezo-element. The Focal volume may in some embodiments refer to a volume of a subject's tissue.

FWHM in this text is defined as the width of the function peak at half of its maximum. The peak of a function may have only positive values (positive phase) or negative values (negative phase). Zero value is determined as a value in a system without supplying the system any kind of energy at the beginning of the measurement, according to the International Standard Metric Conditions. The peak is defined between a first zero value of the function and a second subsequent zero value of the function without changing the phase of the function. The first and the second zero value may be chosen from a plurality of the zero values. The signal noise may not be included in the meaning of individual peaks.

The rise time of a shock wave pulse is the shortest time interval between zero pressure value of the shock wave positive phase peak to its global maximum.

A treatment energy source refers to a part of a device that may provide treatment energy in order to facilitate treatment.

Treatment energy is energy provided to a patient's or subject's body in order to cause treatment effects. Treatment energy may be focused or unfocused, selective or non-selective. Types of applied treatment energy may include, but are not limited to: radio-frequency (RF), light, electric current, plasma, a continuous or time-varying magnetic field, acoustic wave, ultrasound, shock wave, heating, cooling, or applied pressure to the soft tissue of a patient, for example a massage.

A treatment effect is an effect caused by the application of treatment energy to the body or tissue of a patient or a subject. A treatment effect may cause intended metabolic or structural changes in a patient's tissue or cells. Treatment effects may include the treatment of body insufficiencies, injuries, or illnesses, as described in this document.

DETAILED DESCRIPTION

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

In some embodiments, a device of the present invention produces shock waves in order to treat a patient's tissue. As illustrated variously in FIG. 1, a shock wave may include more than one positive and more than one negative phase. Alternatively, a shock wave may include one positive and one negative phase, or a shock wave may include one positive phase of the shock wave, sometimes preceded by slightly decreased pressure in the focal volume before the shock wave is delivered.

Shock waves may be generated by an applicator connected to a base. The base may include one or more of a power supply, a control unit, a cooling system, a user interface, a connecting interface to connect other external devices, or other components understood to be necessary for the function of a typical shock wave generating device.

A power supply of the present invention powers the various electrical components of the apparatus, including but not limited to a condenser which discharges current into a piezo-element of an applicator of the present invention. The condenser may provide electrical voltage in a range from 1 kV to 90 kV, from 2 kV to 50 kV, from 5 kV to 25 kV, or from 7 kV to 15 kV.

Figure 2:
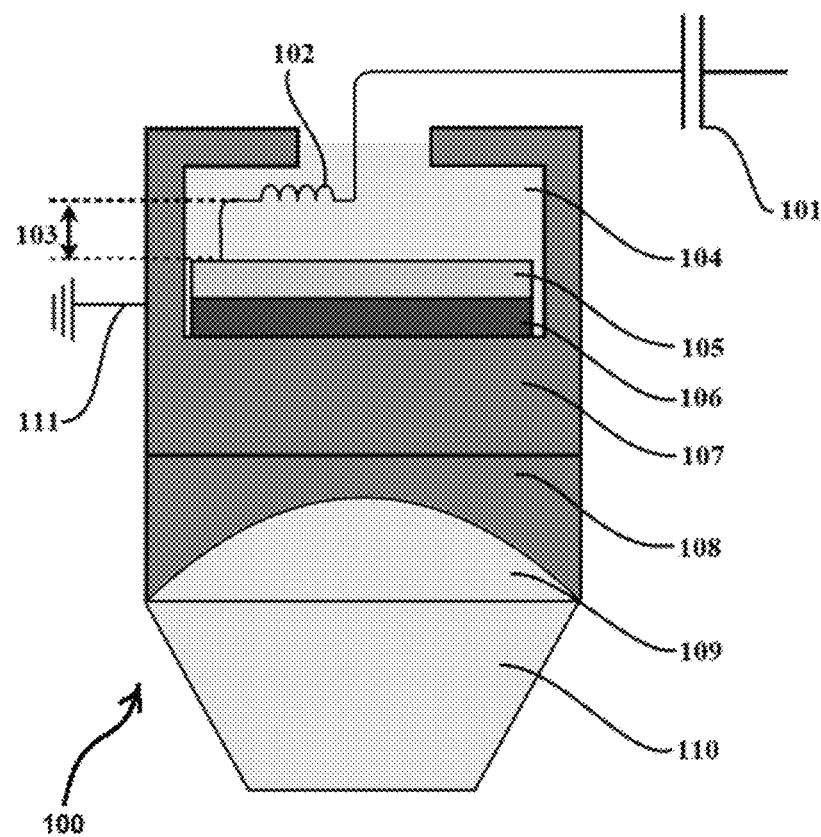
FIG. 2 depicts one of embodiment of an applicator of the present invention.

Referring now to FIG. 2, an applicator 100 may include several divided parts. In some embodiments of the present invention, two or more parts described in this document as separate components may instead be fabricated as one piece.

A piezo-element 106 is powered by a discharging capacitor 101. Electric current from the capacitor 101 goes through a coil 102 connected to a conductive plate 105. The conductive plate 105 may be made of any conductive or semi-conductive material. In some embodiments, the conductive plate 105 may comprise a thin layer of conductive material coated on the piezo-element 106. In some embodiments, the conductive plate 105 may not be included, or may be included in another part of the applicator.

The coil 102 may be spaced apart from the conductive plate 105 by a spacing distance 103 that may be defined for example by at least one nonconductive spacer ring or nonconductive material, for example epoxide. The conductive plate 105 attached to the piezo-element 106 redistributes electric charge across the surface of the piezo-element 106. The piezo-element 106 may be attached to an applicator cell 107. The applicator cell 107 may be grounded, for example by a discharging cable 111. The discharging cable may also be connected to the piezo-element 106 or preferably to the conductive plate 105. The discharging cable reduces resonant effects on the piezo element 106 after the shock wave is generated. A cavity 104 of the applicator cell 107 may be filled by a material e.g.: a material based on epoxide; that may fix all the components in the applicator cell cavity 104 in a static position. For example, the piezo-element 106 may be attached to the applicator cell 107, the conductive plate 105 may be attached to the piezo-element 106, and the inductance element 102 e.g. the coil; may be fixed at specific spacing distance 103 from the conductive plate 105 or from the piezo element 106. Also, the connection between the conductive plate 105 and the piezo-element 106 or the connection between the piezo-element 106 and the applicator cell 107 may be provided by a thin layer of material, for example epoxide. The applicator cell 107 may be attached to an acoustic lens 108, in order to focus the shock wave(s) generated. The acoustic lens 108 may be connected to applicator pad that may have a lower part 109 and an upper part 110.

Currently-used devices with small piezo-elements decrease in effectiveness during their lifetime, as detailed in the background of the invention. According to the experimental tests, a large piezo-element used in accordance with systems and methods of the present invention is able to preserve nearly constant effectiveness during its lifetime.

Mechanical forces caused by electric current acting on the piezo-element increase with the increased volume and diameter of the piezo-element. Higher mechanical forces acting in the piezo-element may tear the piezo-element apart. To prevent damage to the piezo-element, systems of the present invention include certain materials fixing the piezo-element in the cavity. These materials may include materials used to fix the piezo-element to surrounding parts, or in some embodiments include a material partially or completely filling the cavity 104. The material or materials used to fix the piezo-element and surrounding parts in the cavity is selected based on specific mechanical and electrical parameters.

The piezo-element 106 or the conductive plate 105 may be fixed in the applicator cell 107 by a material that may also fill cavity 104, as illustrated in FIG. 2. The material or materials used may include for example epoxide, or may have a dielectric constant in a range from 1.0005 to 2000 or from 1.1 to 150 or from 1.2 to 100 or from 1.2 to 80 or from 1.5 to 8, from 2 to 6, or from 3.5 to 4 with dielectric strength in a range from 1 kV·mm$^{-1}$ to 90 kV·mm$^{-1}$, from 15 kV·mm$^{-1}$ to 60 kV·mm$^{-1}$, or from 25 kV·mm$^{-1}$ to 30 kV·mm$^{-1}$, under the electromagnetic field with frequency 50 Hz and temperature 298.15 K.

In some embodiments, the material selected to fill the cavity 104 influences the durability of the piezo-element. Material with the wrong tensile or flexural strength can cause damage to or destruction of the piezo-element after several pulses, or may cause improper shock wave energy transfer between parts of the applicator. As contemplated herein, materials used to fill the cavity may have flexural strength in a range from 10 MN·m$^{-2}$ to 500 MN·m$^{-2}$, from 40 MN·m$^{-2}$ to 300 MN·m$^{-2}$, from 90 MN·m$^{-2}$ to 110 MN·m$^{-2}$. In some embodiments, tensile strength of such materials are in a range from 10 MN·m$^{-2}$ to 300 MN·m$^{-2}$, from 20 MN·m$^{-2}$ to 150 MN·m$^{-2}$, or from 40 MN·m$^{-2}$ to 60 MN·m$^{-2}$.

Materials used for fixing the piezo-element 106 or filling the cavity 104 may have an acoustic impedance in a range from 0.9·10$^6$ kg·m$^{-2}$·s$^{-1}$ to 6·10$^6$ kg·m$^{-2}$·s$^{-1}$, from 1.5·10$^6$ kg·m$^{-2}$·s$^{-1}$ to 4·10$^6$ kg·m$^{-2}$·s$^{-1}$, or from 2.5·10$^6$ kg·m$^{-2}$·s$^{-1}$ to 3.5·10$^6$ kg·m$^{-2}$·s$^{-1}$.

The epoxide-based materials described above may have properties that protect larger piezo-element against damage from and wear and tear. In some embodiments, a piezo-element fixed with such materials is able to generate up to 10$^6$ shock wave pulses without significantly lowered efficiency.

In some embodiments, such materials may be used to attach the conductive plate 105 to the piezo-element 106, or to another part of the applicator.

Figure 3:
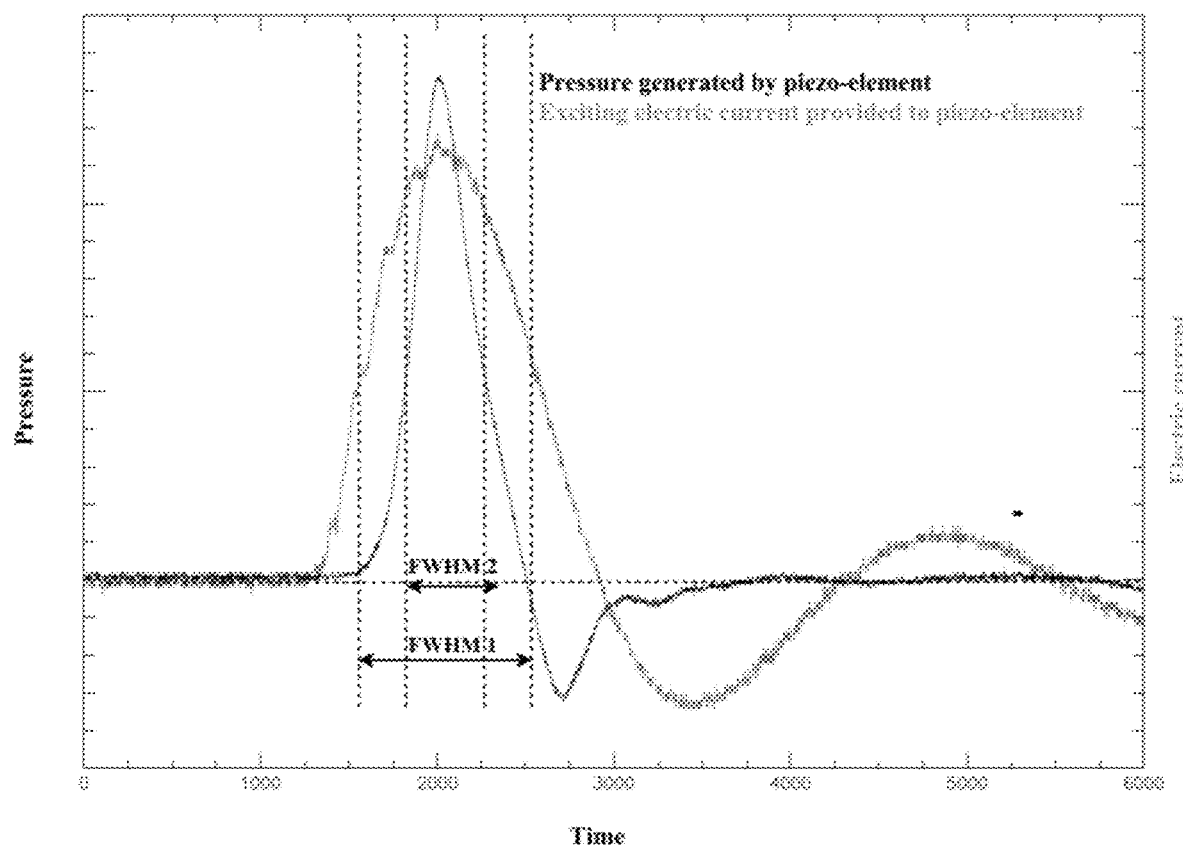
FIG. 3 depicts a graph with respect to time of electric current provided to the piezo-element and the resulting pressure created by the piezo-element in one embodiment of the present invention.

The coil 102 may be located in the applicator or outside of the applicator, for example in the base. The inductance element 102 e.g. coil may also be replaced with any part of the device having an inductance up to 1 pH, connected in series connection with a condenser providing one or more electric pulses, and a piezo-element generating one or more shock waves. The coil may be replaced with one or more wires, one or more conductive or semi-conductive elements having the specifications described above, or one or more coils of different sizes and designs. The coil inductance may change the characteristics, for example the duration or the magnitude, of the pulse of electric current transmitted to the piezo-element. This in turn may also change the characteristics of the pressure generated by the piezo-element. As shown in FIG. 3, changing the shape of the electric current pulse provided to the piezo-element may change the size, shape, depth or volume of the shock wave focal volume.

The electric pulse provided from the capacitor is typically a high intensity electric pulse with a short period. In some embodiments, the device may extend the period of the electric current pulse using a coil to enable a wider focus volume along one or more axes. In some embodiments, expanding or changing the shape of the focus volume may improve shock wave energy transfer to a patient's body or reduce stress on a patient's tissue. Capacitor discharge may be fast in order to reduce energy loss and wear in the switching component included in the condenser.

As shown in FIG. 3, increasing the inductance of the coil results in increased FWHM 1 of the electric current pulse in the coil 102, and therefore also increases the FWHM 2 of the pulse of pressure exerted by the piezo-element in the focal volume. Increased FWHM 2 extends the duration of the first shock wave pulse or extends the duration of the first positive phase of the pulse, in order to reduce or eliminate harmful tissue stress. The inductance value of the coil may influence the magnitude of the pressure rising from the positive shock wave phase. The electric current and pressure shock wave graphs over time depicted in FIG. 3 also exhibit decreased peak values with increased coil inductance. Experiments have shown that the shock wave energy delivered to patient's body by a system using a piezo-element with a serially connected coil may be equal to or higher than the shock wave energy delivered to a patient's body by system without a coil. Changing the inductance element 102 (e.g. coil) inductance, for example by changing the spacing distance 103, modulates the electric current pulse function which in turn also changes the size, shape or localization of the shock wave focus volume. Such an arrangement allows practitioners to change the focus volume, shape, or localization without needing to change applicator head. This advantageously may enhance the treatment effects, accelerate treatment, or allow more tissue structures may be treated during a single treatment.

In some embodiments, the FWHM of the pulse width of the first electric current pulse provided to the piezo-element may be in a range from 0.05 µs to 30 µs or from 0.5 µs to 20 µs, or from 0.8 µs to 10 µs.

In some embodiments, the inductance element (e.g. the coil) may have an inductance in a range from 1 µH to 6 mH, from 3 µH to 6 mH, from 5 µH to 1 mH, from 5 µH to 500 µH, from 5 µH to 200 µH or from 15 µH to 200 µH.

The electric current in the coil may be in range from 10 A to 1 kA or from 20 A to 300 A or from 50 A to 150 A during at least part of process when the electric current is provided to piezo-element.

The coil inductance may be influenced by positioning a quantity of material in proximity to the coil, for example a material that is conductive, paramagnetic, diamagnetic or ferromagnetic. For example, if a ferromagnetic material is near a planar coil, the inductance of the coil will be increased. Also, the orientation of the coil with respect to the conductive, paramagnetic, ferromagnetic, or diamagnetic material; or a secondary source of electric or magnetic field may change the inductance of the coil or the effect the coil has on the flow of electric current. Secondary sources of electric or magnetic fields may also influence the piezo-element during the resulting generated shock wave.

According one embodiment, as shown in FIG. 2, the inductance element 102 may be spaced apart from the conductive plate 105 by a distance 103. If the conductive plate 105 isn't included, the inductance element 102 may be spaced from the piezo-element 106 by spacing distance 103 that may be in a range from 0.1 mm to 10 cm, from 0.5 mm to 5 cm, or from 0.5 mm to 3 cm. In some embodiments, the conductive plate 105 is made of for example dural, and may decrease the inductance of the inductance element 102. Decreasing the inductance of the coil, for example by decreasing the spacing distance 103 between the coil and conductive layer will adjust the characteristics of the electric current pulse for the piezo-element before or during the treatment. In some embodiments, the spacing distance 103 is adjustable before, or after treatment.

A treatment protocol according to one embodiment of the present invention may change the orientation or the spacing distance 103 of at least the inductance element (e.g. coil) 102 in the applicator during one treatment, thereby enabling shock wave treatment of different tissue structures in a defined manner without moving the applicator.

In some embodiments, the inductance of the inductance element 102 (e.g. coil) may be adjusted before or during a treatment by changing the coil geometry, for example by changing the winding diameter of the coil or by changing the distance between windings in the coil, sometimes referred to as the inter-winding gap.

In some embodiments, the coil may comprise multiple coils that each may have different inductance, design, or may be oriented in a different direction from one other. In some embodiments, the coil may comprise multiple coils, some or all of which are substantially identical. In such embodiments, one or more coils may be connected to or disconnected from the electrical circuit, or may be moved with respect to one another, for example by changing their orientation, during a treatment in order to modify the electric current pulse provided to the piezo-element.

According to still another embodiment, the inductance of the coil may be adjusted by positioning a quantity of flowing fluid in proximity to the coil, for example a ferromagnetic fluid, where the temperature or flow rate of the fluid is controllable, and may therefore affect the characteristics of the coil and thus the electric current provided to piezo-element.

Coils of the present invention may have different sizes, shapes or designs. A coil may be a planar spiral coil, a solenoidal coil or the coil may comprise one or more non-coil elements having an inductance up to 1 µH, serially connected between the piezo-element and power supply, for example a condenser.

The piezo-element 106 of the device may be of different sizes or shapes. The piezo-element may have the shape of a circular or elliptical disc, a block, a cube, a spiral, or a wavy or pointy surface. In some embodiments, the shape of the piezo-element may be at least partly spherical or the piezo-element may have different shape as appropriate for the design.

As was mentioned above, in some embodiments, larger piezo-elements have better durability and effectiveness during their lifetime.

In some embodiments, the piezo-element may have a volume of at least 1.5 cm$^3$, or may have a volume in a range from 1.5 cm$^3$ to 600 cm$^3$, from 1.5 cm$^3$ to 300 cm$^3$, from 1.5 cm$^3$ to 160 cm$^3$, from 1.5 cm$^3$ to 950 cm$^3$, from 1.5 cm$^3$ to 60 cm$^3$, from 3.5 cm$^3$ to 35 cm$^3$, or from 3.5 cm$^3$ to 20 cm$^3$.

The diameter of the piezo-element may be in a range from 1 cm to 20 cm, from 2 to 15 cm, or from 6 cm to 10 cm.

The frequency of the provided exciting electric current to the piezo-element may be in a range from 1 Hz to 40 Hz, from 2 Hz to 30 Hz, from 2 Hz to 20 Hz, from 2 Hz to 15 Hz, or from 4 Hz to 14 Hz.

The duration of one shock wave pulse may be in a range from 200 ns to 30 µs, from 400 ns to 15 µs, or from 400 ns to 2.5 µs or from 800 ns to 1.5 µs. The FWHM of the shock wave positive phase may be from 50 ns to 20 µs or from 50 ns to 10 µs or from 50 ns to 2.5 µs, from 100 ns to 1.7 µs, or from 100 ns to 1.2 µs.

The pulse width of a shock wave pulse positive phase may be in a range from 0.1 µs to 30 µs, from 0.5 µs to 10 µs, from 0.5 µs to 3 µs, from 0.7 µs to 2 µs, or from 0.8 µs to 1.7 µs.

The rise time of a shock wave pulse may be in a range from 50 ns to 2000 ns, 50 ns to 1000 ns, or from 100 ns to 700 ns, or from 100 ns to 500 ns or from 100 ns to 400 ns.

In some embodiments, an applicator of the present invention may provide a pressure to the patient's body in a range from 5 MPa to 250 MPa, from 5 MPa to 200 MPa, from 5 MPa to 150 MPa, from 5 MPa to 120 MPa, from 8 MPa to 50 MPa, or from 10 MPa to 35 MPa in the focal volume.

The width of the focus volume at the horizontal maximum focal volume cross section (x- or y-axis) may be in a range from 0.1 mm to 100 mm, from 0.5 mm to 70 mm, from 1.5 mm to 50 mm, from 1.5 mm to 40 mm, from 1.5 mm to 15 mm, or from 2 mm to 10 mm. A depth of the focus volume at the vertical maximum focal volume cross section (z axis) may be in a range from 0.1 mm to 100 mm, from 1.5 mm to 100 mm, from 5 mm to 100 mm, from 10 mm to 60 mm, or from 15 mm to 40 mm.

A propagating acoustic wave carries energy. The amount of acoustic energy per unit area is called the energy flux, energy density, energy flux density, the pulse intensity integral or the energy of the shock wave. The IEC standard calls this the "pulse intensity integral (energy density)" and it can be calculated by the following integral:

$$PII = \int p_a u_a dt$$

where $p_a$ is the acoustic pressure and $u_a$ is the particle velocity. The integration is done over the duration of the pulse. This is the acoustic equivalent of the expression from physics "work equals force times distance," where acoustic pressure is the force per unit area and the time integral of the velocity gives the distance.

The units for the pulse intensity integral (PII) are joules per square meter (J/m$^2$). For a progressive wave, we know that the particle velocity is related to the acoustic pressure $u_a = p_a/Z_0$, where $Z_0$ is the specific acoustic impedance of the environment and therefore:

$$PII = \int \frac{p_a^2}{Z_0} dt$$

in which case, one only need measure the pressure of the wave to determine the PII. Note that to calculate the integral, one needs to be able to accurately measure the entire pressure-versus-time waveform so that the integration can be done. The duration of a shock wave pulse, for which this integral needs to be evaluated, is defined as the time from when the absolute value of the pressure first exceeds 10% of the peak pressure until the last time it exceeds 10% of the peak pressure. To determine the energy in an acoustic wave, a specific area, A, has to be chosen, and the energy that passes through that area can then be calculated as:

$$E = \iint PII \, dA$$

where the double integral indicates a surface integral over the surface A. The unit for energy is joules (J). The energy, E, will depend on both the size of the surface A and how the intensity varies across the surface. The focal acoustic pulse energy is calculated using the area in the focal plane, where the pressure is greater than half the maximum pressure (this is equivalent to the focal zone, see below). Energy can also be calculated over different areas, for example where the peak pressure is above 5 MPa.

The energy of the shock wave pulse in at least part of the focal volume measured in water by needle hydrophone may be in a range from 0.01 mJ·mm$^{-2}$ to 20 mJ·mm$^{-2}$, 0.01 mJ·mm$^{-2}$ to 15 mJ·mm$^{-2}$, 0.01 mJ·mm$^{-2}$ to 10 mJ·mm$^{-2}$ from 0.01 mJ·mm$^{-2}$ to 7 mJ·mm$^{-2}$, from 0.03 mJ·mm$^{-2}$ to 4 mJ·mm$^{-2}$, or from 0.03 mJ·mm$^{-2}$ to 0.5 mJ·mm$^{-2}$ in the focus volume.

The size, shape or depth of the focal volume may be influenced by acoustic lens 108. The acoustic lens radius of curvature may be in a range from 30 mm to 350 mm, from 30 mm to 150 mm, from 40 mm to 100 mm, or from 50 mm to 80 mm.

The acoustic impedance of the acoustic lens 108, the applicator cell 107, or the conductive plate 105 may be in a range from 10·10$^6$ kg·m$^{-2}$·s$^{-1}$ to 46·10$^6$ kg·m$^{-2}$·s$^{-1}$, from 10·10$^6$ kg·m$^{-2}$·s$^{-1}$ to 30·10$^6$ kg·m$^{-2}$·s$^{-1}$ or from 15·10$^6$ kg·m$^{-2}$·s$^{-1}$ to 22 kg·m$^{-2}$·s$^{-1}$. The acoustic lens 108, the applicator cell 107, or the conductive plate may be for example composed of dural, stainless steel, ceramic, alloys, or polymeric materials: e.g. plastic materials and/or other.

According one embodiment using parameters described above, the device and/or method may be able generate multiple shock wave pulses by one exciting electric current provided to a piezo-element, see FIG. 1. FIG. 1 illustrates one possible type of shock waves pulses. The first shock wave represented by the first positive phase peak may have lower energy than the second shock wave represented by the second positive phase peak. According to different configurations of the applicator, the second shock wave may have a lower maximal pressure value than the first shock wave. The first and the second shock waves may be chosen from multiple positive phase peaks.

Differences between maximal pressure values of the first and the second shock wave may be in a range from 10% to 2000% or from 20% to 1000% or from 30% to 500% or from 40% to 300%.

The time interval between the maximal pressure value of the first and the second shock wave may be in range from 100 ns to 10 μs or from 200 ns to 4 μs or from 500 ns to 4 μs or from 800 ns to 3 μs.

Two or more subsequent shock waves generated by one exciting electric current provided to a piezo-element improves treatment results, shock wave penetration into soft tissue, and focus of the shock wave, and may enable treatment of different tissue structures in different depths at one time and/or may improve energy transfer into a patient's tissue. Currently used shock wave treatment devices are not able to produce two or more shock waves with such short time intervals between peaks of the shock waves.

Figure 4:
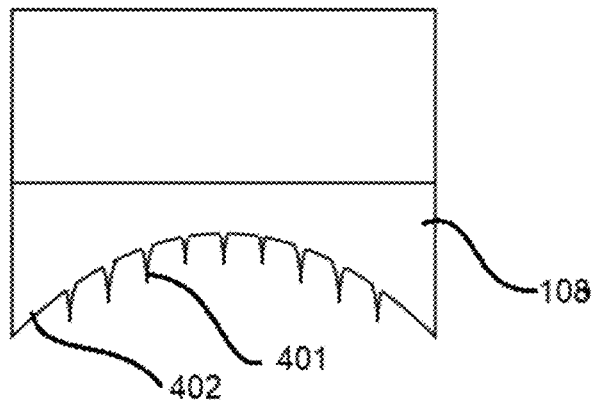
FIG. 4 depicts one embodiment of an acoustic lens with a jagged surface.
Figure 5:
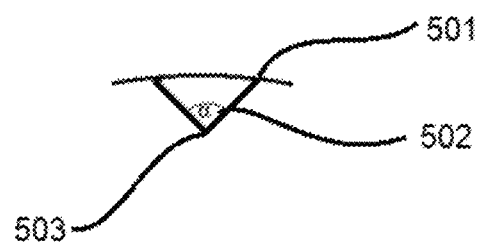
FIG. 5 depicts one embodiment of an acoustic lens with a V-shaped ring on the surface.

According to one embodiment, the pressure energy transfer to the patient's body may be enhanced by the specific surface shape of the acoustic lens 108. The Acoustic lens may create convergent and/or divergent focal volume. The acoustic lens may be at least partially convex, at least partially concave, may be flat and/or may have other different shape and surface modifications. The acoustic lens may have a jagged surface. As shown in FIG. 4, one or more teeth, pins, or protrusions 401 on the surface 402 of acoustic lens 108 may have different sizes and shapes. As shown in FIG. 4, an acoustic lens surface 402 may comprise a plurality of individual teeth or may instead comprise V-shaped concentric rings 401. The one or more V-shaped concentric rings may be spaced by 0.5 to 5 mm, or may alternatively continually merge into one to another. The one or more V-shaped protrusions may have a height in a range from 0.5 mm to 5 mm, from 1 mm to 4 mm, or from 2 mm to 3 mm from the acoustic lens surface 501. As shown in FIG. 5, the angle α 502 in the top 503 of a V-shaped protrusion may be in a range from 90° to 20°, from 90° to 50°, or between 90° to 70°. V-shaped protrusions may have a rounded toe or have a convex or concave profiling.

According to one embodiment, a v-shaped protrusion as shown in FIG. 5 has a height and/or a width that is less than is the shock wave length.

In another embodiment, an acoustic lens may comprise one or more concentric grooves, for example like the profile of a pagoda. Concentric rings or grooves may create patterns resembling pyramids, prisms or other protrusions on the acoustic lens surface.

Protrusions on the acoustic lens surface may improve the energy transfer of the shock wave from the applicator to the patient's body because of a spacing between protrusions that simulates an environment with continually merging acoustic impedance during acoustic wave transmission. The effectiveness of acoustic wave energy transfer may also be enhanced by the Huygens principle and by multiple reflections of the acoustic (shock) wave(s) on the protrusions 401.

Protrusions 401 on the surface 402 of acoustic lens 108 may also modify the shape or volume of the energy focus spot. Protrusions may extend the horizontal focus volume area, increase the focus volume or defocus the shock wave.

According to one embodiment, optimal protrusions 401 may be overlaid by an additional layer characterized by higher stiffness than the material of the applicator pad, e.g. by a layer of hard polyurethane with shore in range from A40 to A95 or from A50 to A95 or from A60 to A95.

According to one embodiment, one or more applicator parts e.g. the acoustic lens 108, the applicator pad that may be divided into an applicator pad lower part 109 or an applicator pad upper part 110 may be an exchangeable part that may be exchanged before and/or during the treatment.

Changing the height, shape or material of the applicator pad upper part 110 and/or the applicator pad lover part 109 may change the size, shape and/or the depth of the shock wave focal volume in the patient's tissue. The applicator pad upper part 110 and/or the applicator pad lower part 109 may be also be used as a wave guide and modulate the produced shock waves. The rigidity of the upper part 110 may also improve energy transfer to the patient's body or increase the comfort of the treatment. In another embodiment, the applicator pad upper part 110 and the applicator pad lower part 109 may be designed as one piece and may be made from the same or different materials.

The applicator pad upper part 110 and/or the applicator pad lower part 109 may be made from a flexible material, but in some embodiments the parts may be made such that they preserve their fabricated shape without the need for any other protecting layer, for example a bag. The applicator pad lower part 109 and/or upper part 110 may be fabricated from a variety of materials, including but not limited to: metal alloys, silicon, silicone, ballistics gel, different polyurethane, ERAGEL, and/or other materials. Materials in contact with the patient's skin preferably have approximately the same acoustic impedance as that of the patient's soft tissue. The applicator pad upper part 110 and/or the applicator pad lower part 109 may be made from more than one polymer and/or material with different rigidity, acoustic impedance, tensile flexural strength and/or other properties.

The applicator pad upper part 110 and the applicator pad lower part 109 may change focus and/or defocus of the treatment energy source like e.g.: shock wave, radiofrequency treatment energy source, light and/or other. One or more layers and/or element(s) in the lower part 109 and/or upper part 110 may be designed from different materials e.g. epoxy, polyurethane gel with different acoustic impedance, rigidity, flexural and/or tensile strength.

According to one embodiment at least one part of applicator pad may be made of polyurethane gels with shore from OO-09 to A95 or from OO-10 to A95 or from OO-10 to A80 or from A10 to A60. An applicator pad may also include other additives like e.g. a UV stabilizer Tinuvin, with a shore durometer value in a range from B 60 to B 80.

An acoustic lens 108 may be covered by one or more additional layers located between acoustic lens 108 and the patient's surface. One or more additional layers may be deposited on acoustic lens 108 separately from any applicator pad and/or may be part of the applicator pad lower 109 and/or upper 110 part. Such layers may prevent oxidation of the acoustic lens 108 (e.g. a layer made of epoxy), may improve resonance of generated acoustic wave e.g. shock wave, may improve energy transfer to patients' bodies and/or may increase durability of the acoustic lens. Additional layers may be part of the applicator pad lower and/or upper part.

According to one embodiment, one or more additional layers may be arranged in a manner so as to minimize the difference between acoustic properties of the acoustic lens and the patient's body to prevent reflection of the acoustic (shock) wave from interface of different acoustic environments. According to another embodiment, one or more additional layers may supplemented by the applicator pad with different acoustic properties of the applicator pad near acoustic lens 108 than acoustic properties of the applicator pad near the patient's body.

According to one non-limiting example, an additional layer closer to acoustic lens 108 may have higher acoustic impedance with higher rigidity than the applicator pad closer to the patient's body.

According to another embodiment, one additional layer may have thickness in a range from 0.1 mm to 14 mm or from 0.5 mm to 10 mm.

According to another embodiment, an applicator pad may include one or more defocusing elements that may be used to defocus or magnify focus volume. The defocusing element may be any design as an additional layer and/or any object located between acoustic lens 108 and patient's body. A defocusing element may be any part of the layer and/or object located in the direction of spreading of acoustic wave (e.g. shock wave). A defocusing element may be characterized by different acoustic impedance (e.g. higher) in the direction of the spreading acoustic wave than the material in proximity to defocusing element. At least part of the applicator pad (upper/lower part) may have resulting rigidity in a range from OO-09 to A95 or from OO-10 to A95 or from OO-10 to A80 or from A10 to A60 or from B 60 to B 80. An average acoustic impedance of upper part 110 or lower part 109 may be in a range from $0.5 \cdot 10^6$ kg·m$^{-2}$·s$^{-1}$ to $6 \cdot 10^6$ kg·m$^{-2}$·s$^{-1}$, or from $0.6 \cdot 10^6$ kg·m$^{-2}$·s$^{-1}$ to $3.5 \cdot 10^6$ kg·m$^{-2}$·s$^{-1}$, or from $0.7 \cdot 10^6$ kg·m$^{-2}$·s$^{-1}$ to $1.8 \cdot 10^6$ kg·m$^{-2}$·s$^{-1}$. The acoustic impedance of at least part of applicator pad (upper/lower part), calculated as the product of speed with density may be in a range from 1.1 to 2.1 (MRayl) or from 1.4 to 1.8 (MRayl) or from 1.5 to 1.75 (MRayl).

Different applicator heads may be used for specific patient or treatment needs. Changing the acoustic lens curvature, materials, surface profiling, the acoustic lens size, the piezo-element size, or making any other modification may change the size, shape, or depth of the focal volume, or also the intensity of the delivered shock wave energy. Such adjustments may further consequently improve the energy transfer, the ability to collect feedback data, or other properties.

According to one embodiment, functionality of the piezo-element may be electronically tested before, during and/or after the treatment. A broken piezo-element is detected when measured electric current and/or voltage provided to the piezo-element has a different profile of measured value during the time than is the expected (reference) signal. Sensors used to measure piezo-element functionality may include a sensor measuring electric current, voltage, pressure, magnetic field, size changes of piezo-element, sensor measuring tensile force and/or other sensor.

According to one preferred but not limiting embodiment, piezo-element functionality may be measured between the acoustic lens and an inductance element.

In one embodiment, the treatment head may be exchanged during treatment, with only the upper part 110 and the lower part 109 remaining attached to the acoustic lens 108 and the rest of applicator.

According to another embodiment the acoustic lens 108, applicator pad upper part 110 and/or applicator pad lower part 109 may be exchanged.

In another embodiment, the upper part 110 and the lower part 109 may be manufactured as a single piece.

Replacement of applicator parts may be facilitated by fixing various parts together using, for example, screwthreads, a clamp mechanism, or some other fastening mechanism. Some exchangeable parts may be fastened to the applicator by a fastening mechanism based on magnetism, electromagnetic forces, or another mechanical fastening mechanism, for example a connector or a clamp mechanism. In some embodiments, two parts of the device of the present invention are fastened together via inserting at least part of one part into another part, based on an interlocking design.

In some embodiments, a changed part and its specifications may be automatically recognized by the applicator, the base, or another connected external device. Examples of such hot-swappable auto-detection mechanisms are described in U.S. patent application Ser. Nos. 15/584,747 and 15/678,915, both of which are incorporated herein by reference in their entireties.

In another embodiment, the applicator may include a shock wave treatment energy source and one or more other treatment energy sources based on e.g.: light, ultrasound, plasma, heating, cooling element, electrotherapy, magnetic fields and/or radio-frequency.

According to one embodiment, the temperature of one or more of the upper part 110, the lower part 109, the acoustic lens 108, the applicator cell 107, the piezo-element 106, the conductive plate 105, or other parts of the device may be regulated. The temperature of the part of the applicator in contact with the patient (for example the upper part 110) may influence treatment results. In some embodiments, increasing the temperature of the applicator part in contact with the patient to a range from 36° C. to 42° C. improves blood and lymph circulation and accelerates cell and body metabolism. Increased temperature may have positive results in recovery treatment or removal of adipose tissue.

In some embodiments, the temperature of the applicator part in contact with the patient is decreased to a temperature in a range from 10° C. to 35° C. or from 15° C. to 25° C. Such a decreased temperature in, for example, the upper part 110 may be beneficial during pain reducing treatment, preventing edema or tissue damage.

Additional treatment energy sources may be located in or around the lower part 109 or upper part 110, in an external device, attached somewhere else on the applicator, or incorporated into the applicator. Included additional treatment energy source(s) providing at least one type of treatment energy may comprise for example electric current, plasma, acoustic waves, light, radio frequency field, magnetic field etc. Such secondary treatments may be applied before or during the primary treatment, sequentially or simultaneously with applied shock waves.

For example, a treatment energy source providing light may heat, reduce pain or influence cell metabolism during shock wave treatment, and may therefore have a synergistic effect with the shock wave treatment. Light applied with shock waves may also increase treatment effect during removal of skin color inhomogeneities or destruction of targeted pigments.

According to another embodiment, the applicator may include at least one electrode, for example on the side of the lower part 110. The at least one electrode may provide monopolar, bipolar or multipolar radio frequency treatment, for example heating of tissue. Such treatments may have a synergistic treatment effect, for example in remodeling collagen fibers, removing adipose tissue, removing cellulite, etc.

Heating tissue may also change the acoustic impedance of that tissue, leading to improved targeting of shock wave treatment. In some embodiments, radio frequency treatment energy is used to selectively heat soft tissue structures located beneath the epidermis. Such selective heating may be used to selectively treat specific soft tissue structures using shock waves.

Radio frequency energy, in combination with applied shock waves, may provide excellent treatment results during circumferential reduction therapy, or during adipose cell number or volume reduction therapy. Radio frequency augmented with shock waves may cause cell apoptosis or necrosis, and shock waves may also have the synergistic effect of accelerating lymph and blood flow, leading to accelerated removal of damaged cells. Combined treatments may also be used in some embodiments to prevent panniculus.

An example of radio-frequency heating may be found in U.S. patent application Ser. No. 16/134,116, incorporated herein by reference. Such heating, in combination with acoustic waves and/or shock waves, may have significantly improved treatment results in tissue rejuvenation, regeneration, removing and/or downsizing of adipose tissue and/or during other treatments.

Human skin is tissue which is commonly treated in order to improve its visual appearance. Skin is composed of three basic elements: the epidermis, the dermis and the hypodermis or so called subcutis. The outer and also thinnest layer of skin is the epidermis. The epidermis contains mainly stratified squamous epithelium of which the outer side keratinizes and ensures coverage whereas the inner side contains a pigment. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT).

SWAT is formed by aggregation of fat cells ranging up to 120 microns in diameter and containing as much as 95% glycerides and fatty acids by volume. Overeating and unhealthy lifestyles may result in an increase in the size and/or number of the fat cells. The fat cells create lobules which are bounded by connective tissue, fibrous septa (retinaculum cutis).

Another part of adipose tissue is located in the peritoneal cavity and is known as abdominal obesity. A visceral fat layer forming visceral white adipose tissue (VWAT) is located between parietal peritoneum and visceral peritoneum, closely below muscle fibers adjoining the hypodermis layer.

An excess of adipose tissue in the subcutaneous or abdominal area may be perceived as aesthetically undesirable, mainly in the buttocks, thighs, abdomen or hips, where even weight loss after dieting and exercise may not lead to satisfactory results. Moreover, in the last few decades, more people suffer from growth of visceral white adipose tissue (VWAT) mainly in their abdominal area. Visceral fat has been also linked to various cardiovascular diseases and diabetes.

An undesirable topographic skin appearance may also be caused by changes in the dermal or sub-dermal layer of the skin, especially by an excessive number or volume of fat cells, weakening of fibrous septas, loss of elasticity and/or limited lymph flow, which may result in accumulation of toxins.

An electromagnetic field may be generated by energy delivery elements (e.g. LED, lamps, and a bipolar, monopolar, unipolar, multipolar electrodes) in a direct, indirect or even noncontact arrangement with the skin surface. The electromagnetic field frequency may be in the range from 0.1 MHz to 10 GHz.

Combinations of both therapies provide new soft tissue treatments with reduced risk of adverse effects. Treatments may lead to remodeling of a soft tissue in the skin area including white adipose tissue. Remodeling may include a reduction in number and/or volume of the visceral white adipose tissue and/or the subcutaneous white adipose tissue. Treatments may also lead to improvement of connective tissue elasticity, mainly elasticity of fibrous septae connecting the dermis to the underlying fascia.

The sum of the energy flux density of the mechanical stimulation and the electromagnetic field applied to the patient simultaneously, successively or in overlap is typically above $1 \text{ mW} \cdot \text{mm}^{-2}$. With the simultaneous method, the electromagnetic field and mechanical stimulation are both used simultaneously during the time interval e.g., 1-10 seconds. In the successive method, an electromagnetic field is used during a first time interval of e.g., 1-5 seconds. The electromagnetic field is then stopped and mechanical stimulation is used in a subsequent time interval of e.g., 6-10 seconds (immediately afterwards the electromagnetic field ends, with the combined application time in this example totaling to 10 seconds). In the overlapping method, an electromagnetic field is used during a first time interval from e.g., 1-7 seconds, and mechanical stimulation is used in a second overlapping time interval of e.g., 4-10 seconds (wherein during the second time interval the electromagnetic field and mechanical stimulation are simultaneously applied over the time interval starting at 4 seconds and ending at 7 seconds).

Mechanical stimulation includes acoustic, ultrasound and/or shock waves. Shock waves are waves characterized by steep pressure amplitude growth in comparison to the surrounding pressure. Despite their relationship with other types of mechanical stimulation, shock waves are different mainly in pressure magnitude and in the shape of the pressure wave. In comparison to ultrasound waves where the pressure periodically oscillates with limited bandwidth and amplitude, shock waves are characterized by non-linearity during wave propagation. In the present invention, shock wave propagation is characterized by a swift positive pressure increase in the range from one nanosecond up to 100 microseconds with positive peak pressure amplitudes up to 150 MPa. In comparison, regular ultrasound methods have positive peak pressure amplitudes up to about 3 MPa. The pulse duration (based on the time the pressure exceeds a half value of peak positive pressure) is preferably in the range of hundreds of nanoseconds to tens to hundreds of microseconds.

The electromagnetic field used for heating the soft tissue may be a radiofrequency field or a microwave field, typically in the range of 0.1 MHz to 25 GHz, more preferably in the range from 0.1 MHz to 435 MHz, most preferably in the range from 0.1 MHz to 28 MHz. All the above mentioned waves may cause movement of charged particles e.g. ions, rotation of dipolar molecules or polarization of normally non polar particles and may therefore increase the tissue temperature.

The device for the proposed therapy may include a bipolar electrode system, where electrodes alternate between active and return functions and where the thermal gradient beneath the electrodes is almost the same during treatment. Bipolar electrodes may form circular or ellipsoidal shapes, where electrodes are concentric to each other. However, a group of bipolar electrodes may be used as well. Alternatively, a monopolar electrode system may be used. With the monopolar arrangement, the return electrode has a sufficiently large area in comparison to the active electrode. The return electrode is in contact with the skin of the patient and may by positioned relatively farther from the active electrode. A unipolar electrode may also optionally be used. Both capacitive and resistive electrodes may be used. Optionally one or more inductive electrodes may be used.

One or more multipolar electrodes may be used.

Figure 6A:
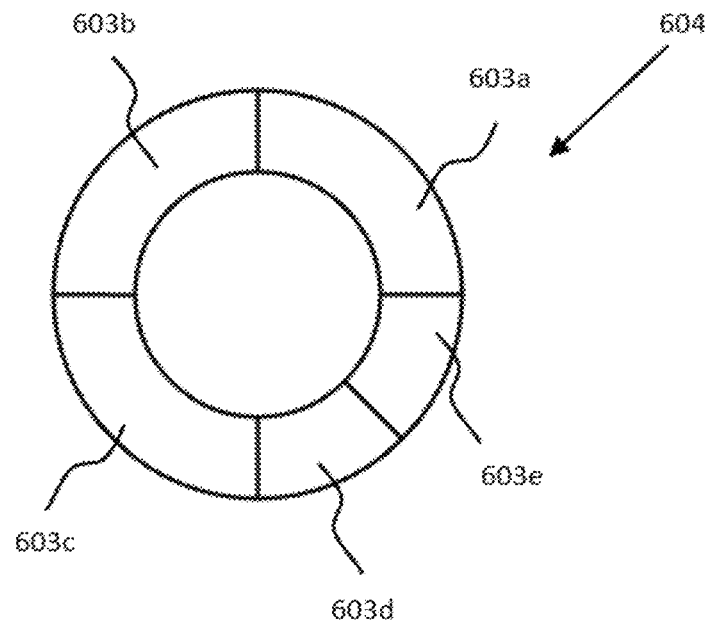
FIG. 6A is a schematic view of a multipolar electrode.
Figure 6B:
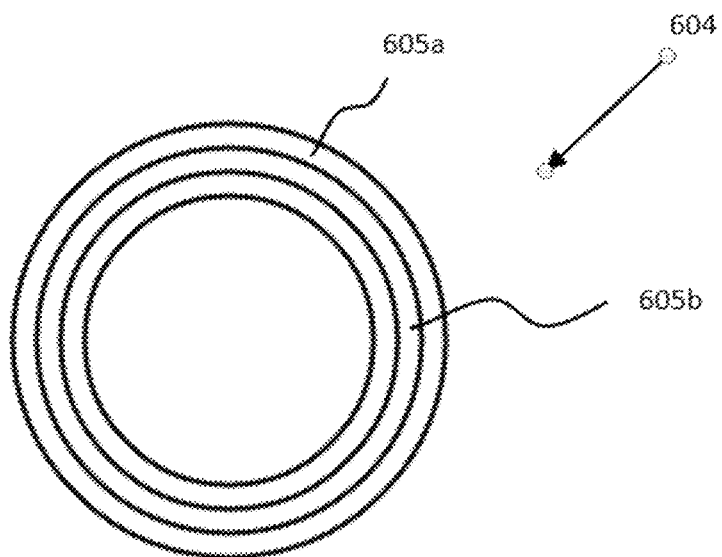
FIG. 6B is a schematic view of another multipolar electrode.

An energy delivery element may be divided into segments to provide treatment to selected parts of the tissue with higher efficiency or in a repeating manner. FIG. 6A shows an energy delivery element divided into two or more segments 603a-e having the shape of an arc. A negative or positive charge of each segment may alternate. Each segment may be operated independently of other segments. Angular sections of the arc may be in the range of 1° to 359° or 5° to 275° to 15° to 185° or 20° to 95°. FIG. 6B shows an energy delivery element 604 divided into two or more segments 605a-b having the shape of layers, which may be concentric to each other.

In order to increase deep tissue heating by the electromagnetic field, the distance between electrodes may be varied; the electromagnetic field may be phase shifted or modulated; or an external magnetic field may be applied.

An energy flux density of the electromagnetic field is preferably in the range between 0.01 mW·mm$^{-2}$ and 10 000 mW·mm$^{-2}$, more preferably in the range between 0.1 mW·mm$^{-2}$ and 5 000 mW·mm$^{-2}$, most preferably in the range between 0.5 mW·mm$^{-2}$ and 1 000 mW·mm$^{-2}$.

The sum of the energy flux density of the mechanical stimulation and electromagnetic field applied to the patient simultaneously, successively or in overlap should be preferably above 0.1 mW·mm$^{-2}$, 1 mW·mm$^{-2}$, or 5 mW·mm$^{-2}$, generally up to a maximum of 100, 500 or 1000 mW·mm$^{-2}$, 5000, 10 000 or 15 000 mW·mm$^{-2}$.

The treatment device may include a transmatch adjusting impedance to the impedance of the treated tissue in order to maximize the power transmission. The transmatch may adjust the impedance in order to minimize the reflected power. The device may also include a balun transformer, which may be part of the transmatch. The balun may allow for treatment without the need for grounding.

Figure 7:
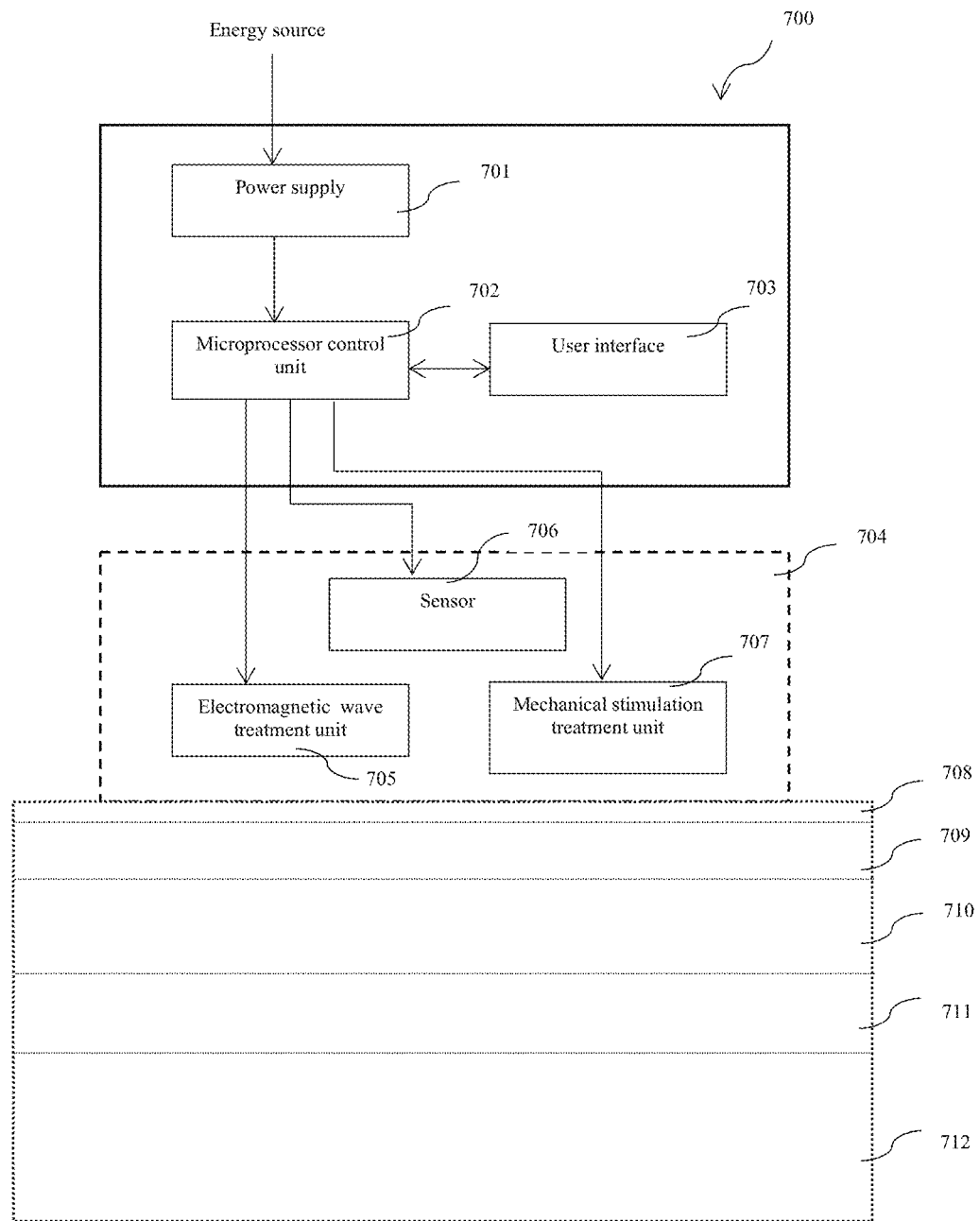
FIG. 7 is a schematic example of positioning of the system for skin treatment.

FIG. 7 shows a schematic example of positioning of the system for skin treatment. The system for skin treatment 700 applies a combination of electromagnetic and mechanical stimulation energy into the soft tissue. The system may include a power supply 701 connected to an energy source. The system for skin treatment 700 includes at least one applicator 704 which may be placed inside a case or may be separated from the system for skin treatment 700 and connected by a cable. The microprocessor control unit 702 with user interface 703 provides communication between the electromagnetic field treatment unit 705 and mechanical stimulation treatment unit 707. User interface 703 allows setting up the treatment parameters and also may provide the operator various treatment information. User interface 703 may include a display. The electromagnetic field treatment unit 705 and mechanical stimulation treatment unit 707 may be placed in at least one applicator 704. However the treatment units may also have separate applicators. The applicator 704 may preferably contain a sensor unit 706.

The output power of the power supply 701 may be in the range of 10 W to 600 W, preferably in the range of 50 W to 500 W, most preferably in the range of 80 W to 450 W.

The sensor unit 706 may contain one or more sensors for sensing temperature, resistance, movement, contact with skin or force applied to skin. The sensor may be invasive or contactless. The sensor may measure one or more physical quantities of the treated tissue and/or untreated tissue.

The temperature sensor measures and monitors the temperature of the treated tissue. Temperature can be analyzed by a microprocessor control unit 702. The temperature sensor may be a contact sensor, contactless sensor (e.g. infrared temperature sensor) or invasive sensor (e.g. a thermocouple) for precise temperature measuring of deep layers of soft tissue. The microprocessor control unit 702 may also use algorithms to calculate the deep or upper-most temperatures. A temperature feedback system may control the temperature based on set/pre-set limits, alert the operator in human perceptible form e.g. on the user interface 703. In a limit temperature condition, the device may be configured to adjust output power, activate cooling or stop the therapy. A human perceptible form may be a sound and/or a change of color of the applicator 704 and/or the tip.

The system for skin treatment 700 generates electromagnetic waves and mechanical stimulation enabling improvement of the soft tissue, mainly connective tissue in the skin area. The connective tissue in the skin area contains epidermis layer 708 and dermis layer 709; white adipose tissue in hypodermis layer 710 and peritoneal cavity 712. The other soft tissue below the skin area e.g. muscular tissue 711 remains untreated and unharmed. The therapy may stimulate blood circulation or may also create micro-disruptions of treated tissue, and/or create movement, rotation or polarization of particles by induced current and/or magnetic field which increase the temperature of the treated tissue. The combined therapy may result in increased cell membrane permeability, which may result in increased liquefying of fat and/or lipolysis. A combination of both therapies greatly reduces the risk of adipocytes inflammation.

Without being bound to the theory, it is believed that the mechanical stimulation may increase the penetration depth and enable remodeling of the visceral white adipose tissue which is located in the peritoneal cavity 712. The mechanical stimulation, in combination with an electromagnetic field, may result in a reduction of visceral fat cells. Therefore the overall number and/or volume of SWAT and/or VWAT may be reduced. The temperature of the treated tissue during the therapy may be increased to about 32-48° C.

Neovascularization may be induced based on increased angiogenic grow factors VEGF, and also PCNA, NOS etc.

Improvements in the microvascular network may also result in better lipid metabolism functionality.

Another soft tissue improvement is in the field of tissue elasticity. The micro-disruptions also lead to improved tissue regeneration and in combination with electromagnetic field therapy induces neocollagenesis, neoelastogenesis and improvement of tissue elasticity. Although neocollagenesis is normally induced at higher temperatures than 32-48° C., the combination of mechanical stimulation with an electromagnetic field enables improved results at temperatures in this range, resulting in less stress of the tissue. The treatment may include at least partial destruction and subsequent repair and/or synthesis of other forms of connective tissue, e.g. fibronectin, matricellular protein etc.

The energy transfer may change attributes of the tissue. The temperature of the tissue may be increased to about 32-48° C.

The electromagnetic field and mechanical stimulation may be applied with a frequency ratio which provides significant results, convenient treatment and minimal adverse effects. The ratio between the electromagnetic field frequency and mechanical stimulation frequency (MHz/Hz) may be in the range of 0.005 to 60 or 0.01 to 28.

Treatments may be performed on the whole surface of the body or may include particular parts of body e.g. face, neck, breasts, shoulders, thorax, abdomen, waistline, genitals, region of love handles, sides of the torso (e.g. bra fat), arms, buttocks, saddlebag, thighs, and calf. Treatment of the face may include treatment of wrinkles, cheek lifting and/or treatment of a crooked nose. Treatment of the neck may include treatment of swelling tissue. Treatment of the arms may include treatment of palms, nails, cuticles, or nail beds. Treatment of the arms may also include treatment of bingo wings. Treatment of the genitals may include treatment of the penis and/or scrotum. Treatment of the breasts may include treatment of the Cooper ligament and/or breast lifting. Treatment of the buttocks may include butt lifting. Treatment of the the body may include treatment of tissue above and/or adjacent to at least one lymph node, wherein treatment of the lymph node may provide lymph flow stimulation, treatment of lymphedema and/or lymph filtering stimulation. The present method and device may be used for treatment of sexual problems e.g. erectile dysfunction. Treatment may be targeted to the cavities of the body e.g. mouth, vagina and anus.

The arrangement of mechanical stimulation treatment unit 707 and electromagnetic wave treatment unit 705 may be in one or more separate applicators 704. Where one applicator is used, the applicator 704 may contain one treatment energy delivery element designed for transmission of mechanical stimulation and electromagnetic waves into the soft tissue. However, the mechanical stimulation treatment unit 707 and electromagnetic wave treatment unit 705 may be designed with separate energy delivery elements organized in concentric, axial symmetrical or non-symmetrical ways.

Applicator 704 includes a surface contacting the tissue including one or more energy delivery elements transmitting electromagnetic waves and one or more energy delivery elements designed to transmit mechanical stimulation. The surface of a first energy delivery element is designed to transmit electromagnetic waves and a surface of a second energy delivery element is designed to transmit mechanical stimulation. The effective surface areas of the first and second energy delivery elements may have different ratios. The surface of a first energy delivery element designed to transmit electromagnetic waves may cover at least 20%, more preferably 30%, still more preferably 35% and more preferably 40% of the applicator's surface contacting the tissue. The surface of the second energy delivery element designed to transmit mechanical stimulation may be described as a percussion guide.

The surface of the second energy delivery element may be at least 0.03 cm$^2$, or in the range of 0.05 cm$^2$ to 50 cm$^2$, more preferably in the range of 0.75 cm$^2$ to 40 cm$^2$, most preferably in the range of 0.1 cm$^2$ to 35 cm$^2$.

Surfaces of energy delivery elements providing electromagnetic field and mechanical stimulation may be in a different ratio, which was found to deliver most of the energy used for treatment. The ratio of the surface of the first energy delivery element providing the electromagnetic field to the surface of the second energy delivery element providing mechanical stimulation may be in the range of 0.01 to 80 or 0.05 to 65 or 0.1 to 50 (with the surface areas referring to the surface area of each element intended to make contact with the skin).

Briefly stated, a method for soft tissue treatment of a patient includes positioning an applicator adjacent to the soft tissue of the patient; transmitting mechanical stimulation into the soft tissue of the patient causing mechanical stimulation of the soft tissue of the patient; transmitting electromagnetic waves from the applicator into the soft tissue with the electromagnetic waves heating the soft tissue; and remodeling soft tissues via the combination of mechanical stimulation and electromagnetic waves. The method may remodel the soft tissue and cause reduction of the VWAT and/or the SWAT; reduction in the number of adipose cells; reduction in the volume of adipose cells; and/or improve connective tissue elasticity or cellulite appearance. The method may also improve elasticity of fibrous septae connecting the dermis to the underlying fascia.

Specific treatment energy sources may be also used to collect diagnostic information. For example, ultrasound may be used detect bones under the applicator, or to detect defects or damage to patient tissue. Such diagnostic feedback can be used in some embodiments to intervene in or adjust a treatment, thereby preventing injury to the patient.

In some embodiments the device includes a hand-held applicator, or may include one or more applicators attached to a patient's body, which in some embodiments can eliminate the need to manually move the applicator(s) during treatment.

In some embodiments, the device may recognize the wear level of an individual base or of one or more applicator parts based on counting the applied therapies, the applied shock waves, or the total treatment time. Wear of electrically powered component may be estimated for example by measuring component impedance as it changes over continued use.

Some embodiments of the device may include a cooling system, a user interface, a connecting interface or a control unit.

A cooling system may be part of the applicator or may be located in the base. A cooling system may cool down an applicator's components, for example the piezo-element or the base components, for example a processor. Cooling systems may be active or passive as described in U.S. patent application Ser. No. 15/584,747, incorporated herein by reference in its entirety.

In some embodiments, a device of the present invention includes a user interface to facilitate communication with a user. The user interface may comprise a touch display and one or more buttons, and may display treatment parameters, warnings or other information to the user. A user may select a treatment using the user interface, and may also adjust treatment parameters or other features. The user interface may in some embodiments be part of the applicator or the base.

In some embodiments, the device may include a connecting interface used to connect the apparatus with one or more external devices, for example other therapeutic devices; controlling devices including but not limited to a tablet, smartphone, or computer; or to communicate with a user, service system, or sale system as described in U.S. patent application Ser. No. 15/678,915 the entire contents of which is incorporated herein by reference. In some embodiments, the connecting interface may comprise a physical connection through a connector, for example a USB, serial, parallel, LAN, or other wired interface. Alternatively, the connecting interface may comprise a wireless connection, for example Bluetooth, wi-fi, infrared, LAN, TCP/IP, or other.

The control unit may communicate with the one or more applicators, the user interface, the one or more external devices or with other parts of the device. The control unit may control or evaluate treatment parameters and information from the sensors, may automatically adjust treatment parameters, or may suggest treatment parameters. Treatment parameters may be suggested based on chosen treatment effect, body part, sex, age, type of connected applicator treatment head, and information received from sensors or other sources.

The physiological results of shock wave treatment are not entirely clear. The shock waves act as transient micromechanical forces that induce perturbations at the cellular level, thereby altering biological activity. An induced shock wave may have treatment effects during treatment of soft tissue expanders in reconstructive surgery, distraction osteogenesis and wound healing in which micromechanical forces promote wound healing through increased cell division, angiogenesis, and release of growth factors in the wound bed.

Mechanical waves may cause geometric changes in the cellular cytoskeleton. External deformations can be transduced to an already "prestressed" or internally balanced cytoskeleton through tensile linkages or cell surface receptors that would initiate a cascade of intracellular events leading to changes in cell activity.

Shock wave therapy promotes expression of macromolecules in wound healing, including VEGF, endothelial nitric oxide synthase, and proliferating cell nuclear antigen. In some embodiments, shock waves are used to treat urolithiasis, chronic pain, bone indication, soft tissue disorders, entheso/tendinopathies with calcifications, skin wounds, and other conditions in humans. Shock wave therapy may be perceived by cell surface receptors through extracellular matrix and fluid effects. Mechanoreceptors, including integrins, ion channels, connexins, or the lipid component of the plasma membrane activation could all possibly be affected by shock waves. Akt-mediated mechanotransduction in fibroblasts has been shown to play a role in hypertrophic scar formation in response to mechanical forces.

Described treatment effects of shock wave therapy may be also used in order to provide collagen remodeling, elastogenesis and neocollagenesis to reduce skin laxity, provide skin tightening and rejuvenation. Applied high pressure shock waves may also disrupt some cell metabolic mechanisms or structures that lead to cell apoptosis or even necrosis that may be used to treat circumferential reduction and to remove of adipose tissue.

Shock waves may stimulate sensory nerve fibers, including nociceptors that produce the somatic sensation of mechanical force, which may explain why some patients treated with shock wave therapy report decreased pain. Clinical studies of shock wave therapy in wound healing suggest that wound cause, size, and chronicity may affect the response to shock wave therapy.

Shock waves may further play an important role in promoting healing in diabetic wounds, injured bones, muscles, ligaments, cartilage, flap necrosis, acute epicondylitis, chronic wounds, and burns. Shock waves may be used to treat urological problems, sexual dysfunctions, impaired blood flow, impaired lymph flow, erythema, swelling, loss of bodily sensation, itching, hematoma, petechiae, skin damage after previous corticoid therapy, pain shoulder, triggerpoints, tibial edge syndrome, cacar calcanei, plantar fasciitis, epicondylitis, achillodynia, and patellar tendinopathy. Shock waves may further be used in removal of adipose tissue, decreasing skin laxity, accelerating neocalagenesis, accelerating elastogenesis, accelerating healing of ligaments, cartilages, injured muscles etc.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A device for shock wave production to treat a patient's body, comprising:
 a condenser and a switch configured to discharge a pulse of electric current with a voltage in a range from 2 kV to 50 kV;
 an applicator comprising:
  an applicator cell providing a cavity;
  at least one coil;
  a conductive plate;
  a single piezo-element coupled to the conductive plate and attached to the applicator cell at a bottom of the cavity;
  a dielectric material positioned in the cavity, fixing the single piezo-element in the cavity; and
  an acoustic lens attached to the applicator cell below the single piezo-element;
 wherein the single piezo element is configured to generate at least one shock wave pulse having a duration in a range from 200 ns to 30 µs in response to the pulse of electric current;
 wherein the applicator is configured to provide pressure to the patient's body in a range from 5 MPa to 250 MPa;
 wherein the dielectric material has a dielectric constant in a range from 1.0005 to 2000 and dielectric strength in a range from 1 kV·mm$^{-1}$ to 90 kV·mm$^{-1}$;
 wherein the single piezo-element has a volume in a range from 1.5 cm$^3$ to 600 cm$^3$; and
 wherein the at least one coil and the conductive plate are separated by a spacing distance.

2. The device according to claim 1, wherein the at least one coil has an inductance in a range from 1 µH to 6 mH.

3. The device according to claim 2, wherein the at least one coil has an adjustable inductance.

4. The device according to claim 2, wherein the at least one coil comprises a plurality of coils; and
 wherein the applicator is configured such that individual coils from the plurality of coils may be connected or disconnected in the circuit.

5. The device according to claim 1, wherein the pulse of electric current is in a range from 10 A to 1 kA.

6. The device according to claim 1, wherein the pulse of electric current has a full width at half maximum in a range from 0.05 μs to 30 μs.

7. The device according to claim 1, wherein the dielectric material has a flexural strength in a range from 10 MN·m$^{-2}$ to 500 MN·m$^{-2}$.

8. The device according to claim 1, wherein the dielectric material has a tensile strength in a range of 10 MN·m$^{-2}$ to 300 MN·m$^{-2}$.

9. The device according to claim 1, wherein the dielectric material has an acoustic impedance in a range of 0.9·10$^6$ kg·m$^{-2}$·s$^{-1}$ to 6·10$^6$ kg·m$^{-2}$·s$^{-1}$.

10. The device according to claim 1, wherein the spacing distance is in the range from 0.5 mm to 5 cm.

11. The device according to claim 1, wherein the rise time of the at least one shock wave pulse is in a range from 50 ns to 2000 ns.

12. The device according to claim 1, wherein the single piezo-element has a diameter of 1 cm to 20 cm.

13. The device according to claim 1, wherein the single piezo-element is configured to generate the shock wave with a focus volume having a maximum horizontal focus volume cross-sectional dimension in a range from 0.1 mm to 100 mm.

14. The device according to claim 1, wherein the at least one shock wave pulse has a focus volume having a maximum vertical focus volume cross-sectional dimension in a range of 0.1 mm to 100 mm.

15. The device according to claim 1, wherein the dielectric material has a flexural strength in a range from 10 MN·m$^{-2}$ to 500 MN·m$^{-2}$;
wherein the dielectric material has a tensile strength in a range of 10 MN·m$^{-2}$ to 300 MN·m$^{-2}$; and
wherein the dielectric material has an acoustic impedance in a range of 0.9·10$^6$ kg·m$^{-2}$·s$^{-1}$ to 6·10$^6$ kg·m$^{-2}$·s$^{-1}$.

16. The device according to claim 1, wherein the acoustic lens has an acoustic impedance in a range from 10·10$^6$ kg·m$^{-2}$·s$^{-1}$ to 46·10$^6$ kg·m$^{-2}$·s$^{-1}$.

17. The device according to claim 1, wherein at least one of the applicator cell, the cavity, the conductive plate, the single piezo-element or the acoustic lens is exchangeable.

18. The device according to claim 1, wherein the acoustic lens has a radius of curvature in a range of 30 mm to 350 mm.

19. The device according to claim 1, wherein a surface of the acoustic lens comprises at least one V-shaped protrusion having an angle α in a range of 90° to 20°.

20. The device according to claim 1, wherein the acoustic lens comprises at least one protrusion, and wherein the at least one protrusion is configured to extend a horizontal focus volume area of the shock wave.

21. The device according to claim 1, wherein the cavity is filled with the dielectric material surrounding the piezo-element and the conductive plate, configured to increase durability of the piezo-element.

22. The device according to claim 1, wherein the single piezo-element has a volume in a range from 3.5 cm$^3$ to 35 cm$^3$.

23. A device for shock wave production to treat a patient's body, comprising:
a condenser and a switch configured to discharge a high voltage pulse of electric current;
an applicator comprising:
an applicator cell comprising a cavity;
a coil positioned inside the cavity and configured to be coupled to the condenser and the switch on an input of the coil;
a conductive plate positioned inside the cavity and connected to an output of the coil;
a large piezo-element having a diameter in a range of 1 cm to 20 cm positioned inside the cavity and coupled to the conductive plate and attached to the applicator cell at the bottom of the cavity;
wherein the cavity is filled with a dielectric material having a dielectric constant in a range from 1.0005 to 2000 and dielectric strength in a range of 1 kV·mm$^{-1}$ to 90 kV·mm$^{-1}$ configured to fix and increase durability of the large piezo-element inside the cavity;
wherein the applicator cell is configured to provide a shock wave in response to the high voltage pulse of the electric current passing through the coil to the conductive plate and the large piezo-element, with a duration of created shock wave pulse in a range of 200 ns to 30 μs; and
an acoustic lens having an acoustic impedance in a range from 10·10$^6$ kg·m$^{-2}$·s$^{-1}$ to 46·10$^6$ kg·m$^{-2}$·s$^{-1}$ and configured to be attached to the applicator cell below the single piezo-element and configured to focus the shock wave pulse to the patient's body such that a pressure delivered to the patient's body is in a range from 5 MPa to 250 MPa.

24. The device of claim 23, wherein the large piezo-element has a volume in a range from 1.5 cm$^3$ to 600 cm$^3$.

25. The device of claim 23, wherein the high voltage pulse is in a range of 10 A to 1 kA with a voltage in a range from 2 kV to 50 kV.

26. The device of claim 25, wherein the high voltage pulse of electric current has a full width at half maximum in a range from 0.05 μs to 30 μs.

27. The device according to claim 23, wherein the large piezo-element is configured to generate the shock wave with a focus volume; and
wherein the energy of the shock wave in at least part of the focus volume is in a range from 0.01 mJ·mm$^{-2}$ to 20 mJ·mm$^{-2}$.

28. A device for shock wave production to treat a patient's body, comprising:
a base comprising a condenser and a switch configured to discharge a pulse of electric current;
an applicator configured to be coupled to the base, the applicator comprising:
an applicator cell with a cavity, the inside of the cavity comprising:
a single piezo-element having a volume in a range of 1.5 cm$^3$ to 600 cm$^3$ and attached to the applicator cell at the bottom of the cavity;
a conductive plate attached to the single piezo-element; and
a coil configured to be electrically connected in a series with the conductive plate and the switch,
wherein the single piezo-element is configured to provide a shock wave in response to the pulse of the electric current passing through the coil to the conductive plate based on a piezoelectric effect;
wherein the cavity is filled with a dielectric material having a flexural strength in a range from 10 MN·m$^{-2}$ to 500 MN·m$^{-2}$ and a tensile strength in a range of 10 MN·m$^{-2}$ to 300 MN·m$^{-2}$, configured to fix and to protect the single piezo-element inside the cavity; and
an acoustic lens having a radius of curvature in a range of 30 mm to 350 mm attached to the applicator cell below the single piezo-element and configured to focus the shock wave pulse to the patient's body;

wherein the shock wave has a full width at half maximum in a range of 0.1 µs to 30 µs and is configured to deliver a pressure to the patient's body in a range from 5 MPa to 250 MPa.

29. The device of claim 28, wherein a repetition frequency of delivery of the shock wave is in a range of 1 Hz to 40 Hz.

30. The device of claim 28, wherein the single piezo-element is configured to generate the shock wave with a focus volume, and wherein a width of the focus volume at a horizontal maximum focal volume cross section is in a range from 0.1 mm to 100 mm.

31. The device of claim 28, wherein the dielectric material has an acoustic impedance in a range of $0.9 \cdot 10^6$ kg·m$^{-2}$·s$^{-1}$ to $6 \cdot 10^6$ kg·m$^{-2}$·s$^{-1}$; and wherein the acoustic lens has an acoustic impedance in a range from $10 \cdot 10^6$ kg·m$^{-2}$·s$^{-1}$ to $46 \cdot 10^6$ kg·m$^{-2}$·s$^{-1}$.

32. The device of claim 28, configured to produce first and second shock waves generated by one excitation electric pulse; and wherein a maximal pressure value of the second shock wave is greater than a maximal pressure value of the first shock wave.

\* \* \* \* \*